United States Patent
Richardson

(10) Patent No.: US 6,712,801 B1
(45) Date of Patent: Mar. 30, 2004

(54) POWDER DISPENSING BABY DIAPER

(76) Inventor: Darryl Richardson, 1416 Smithfield Forest La., Birmingham, AL (US) 35127

( * ) Notice: Subject to any disclaimer, the term of this patent is extended or adjusted under 35 U.S.C. 154(b) by 0 days.

(21) Appl. No.: 09/610,949

(22) Filed: Jul. 6, 2000

(51) Int. Cl.$^7$ ................................................ A61F 13/15
(52) U.S. Cl. ............................ 604/385.06; 604/385.01; 604/359
(58) Field of Search .................... 604/385.06, 385.01, 604/385.26, 385.28, 385.14, 359; D24/126

(56) References Cited

U.S. PATENT DOCUMENTS

| | | | | |
|---|---|---|---|---|
| 3,565,075 A | * | 2/1971 | Jerry et al. ................... | 604/307 |
| 3,691,271 A | * | 9/1972 | Charle et al. ................. | 424/431 |
| 3,875,942 A | * | 4/1975 | Roberts et al. ............... | 604/370 |
| 4,221,221 A | * | 9/1980 | Ehrlich ......................... | 128/284 |
| 4,623,339 A | * | 11/1986 | Ciraldo et al. ................ | 604/359 |
| 4,702,378 A | * | 10/1987 | Finkel et al. ................. | 206/581 |
| 4,743,240 A | * | 5/1988 | Powell .................... | 604/385.13 |
| 4,753,643 A | * | 6/1988 | Kassai ........................... | 604/359 |
| 4,753,647 A | * | 6/1988 | Curtis ........................... | 604/385 |
| 4,790,836 A | * | 12/1988 | Brecher ........................ | 604/359 |
| 4,917,693 A | * | 4/1990 | Terry ........................ | 604/385.1 |
| D343,233 S | * | 1/1994 | Lanmon et al. ............. | D24/126 |
| 5,290,268 A | * | 3/1994 | Oliver et al. ................. | 604/359 |
| 5,304,158 A | * | 4/1994 | Webb ...................... | 604/385.13 |
| 5,582,605 A | * | 12/1996 | Lepie ....................... | 604/385.1 |
| 5,702,379 A | * | 12/1997 | Preiss ....................... | 604/385.1 |
| D412,982 S | * | 8/1999 | Wyatt ........................ | D24/126 |
| 5,998,695 A | * | 12/1999 | Roe et al. .................... | 604/367 |
| 6,454,748 B1 | * | 9/2002 | Ives et al. ............... | 604/385.06 |

* cited by examiner

*Primary Examiner*—Weilun Lo
*Assistant Examiner*—Jacqueline Stephens
(74) *Attorney, Agent, or Firm*—C. Brandon Browning; Sirote & Permutt, P.C.

(57) ABSTRACT

A diaper including a pocket patch for containing a substance such as powder wherein the pocket patch is connected with and adapted to dispense the substance to a surface of the diaper for receiving bodily waste and method of dispensing the substance to the diaper surface including folding the diaper about a crotch area thereof and patting the diaper to facilitate dispensing of the substance.

7 Claims, 2 Drawing Sheets

POWDER DISPENSING BABY DIAPER

FIELD OF THE INVENTION

The present invention belongs to the field of art referred to as apparel and sub-classed disposable diaper.

PRIOR ART

To my knowledge, baby diapers are made in a variety of formats to include being; disposable, moisture shielding, scented, easily applied and extra absorbent. However, the present invention goes beyond the normal functions of a diaper, and reduces the work that is usually required in preparing the recipient, to wear the diaper. The present invention aids in the application of powder to the body of the intended wearer.

The operation and design of the present invention makes it convenient, time saving and economical: There is now no need for a separate powder container, nor holder for the container; freeing up space in an items bag, and also freeing the hands of the applier to wrestle with the sometimes reluctant wearer, thereby, filling a general need for an easily applicable, environmentally friendly (Reducing the need for a Baby Powder Container), self-contained and comparatively inexpensive baby diaper.

OBJECTS AND SUMMARY

Accordingly, it is an object of the present invention to provide a Powder Dispensing Baby Diaper that integrally contains its own powder supply, eliminating the need for an individual bottle container.

Another object of the present invention is to provide an apparatus of the aforementioned type that may be made of natural or synthetic biodegradable materials, having a noticeable environmental impact.

A further object of the present invention is to provide an apparatus of the aforementioned type that is easier to administer to the intended wearer, requiring less human effort and is easily portable.

A still further object of the present invention is to provide an apparatus of the aforementioned type that may be applied to the intended wearer in a more expedient manner, requiring less time for its application than that of the conventional diaper, making it more convenient.

Other objects will become apparent in the following detailed description.

Briefly described, the present invention relates to a powder dispensing baby diaper that houses its own powder substance, thereby making it completely self-contained, environmentally friendly, much easier to administer than conventional diapers, relatively inexpensive and a time saver. The present invention is really a "Baby Care Diaper System", suggesting the addition of other diaper administering items such as packeted moisturized baby wipes and lotions. Contained in a single diaper, the present invention is economical and comparatively simple to manufacture.

DETAILED DESCRIPTION

Figure 1:
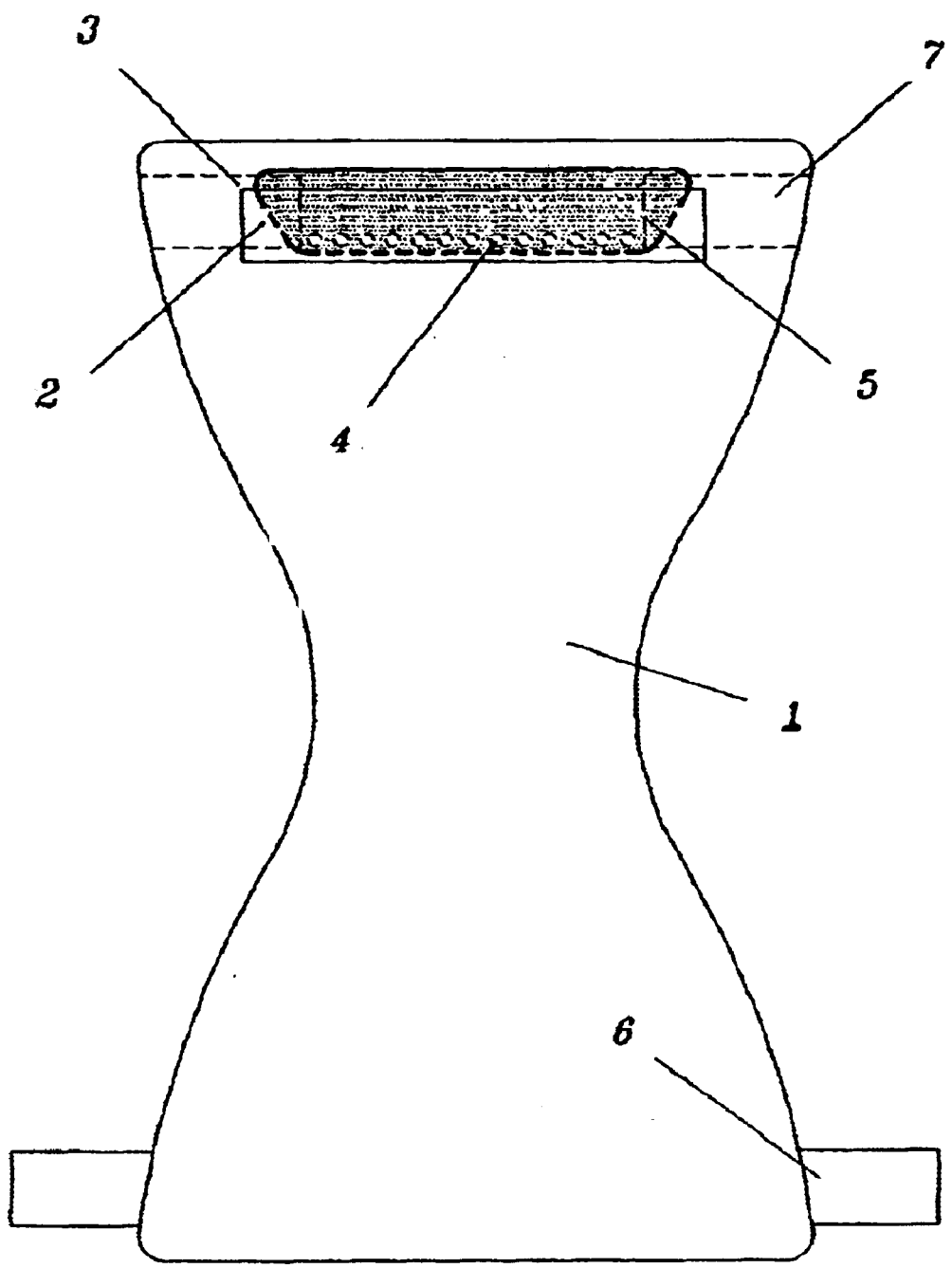
FIG. 1 is a top plan view of a powder dispensing baby diaper according to a preferred embodiment of the present invention.
Figure 2:
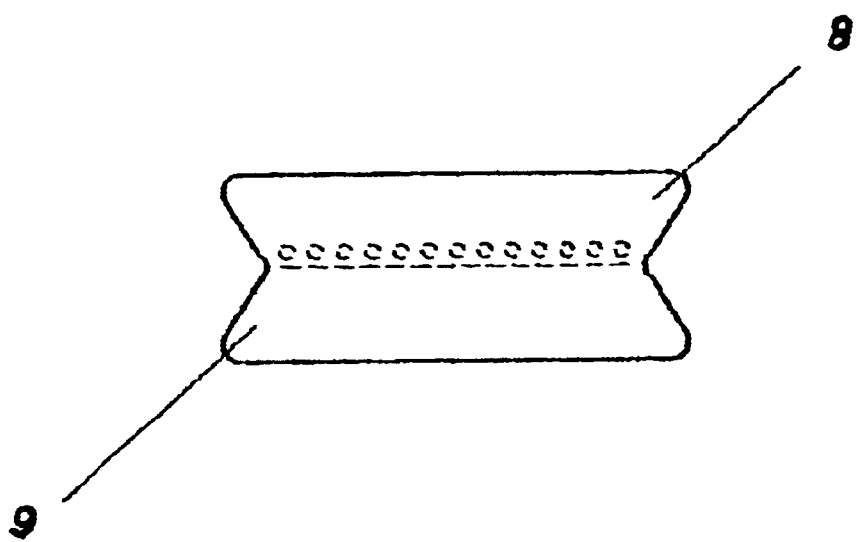
FIG. 2 is a top plan view of the powder patch of FIG. 1 in an unfolded arrangement.

Referring now in detail to the drawings for the purpose of illustrating the present invention, the operational theory and an assembly method are as follows:

Referring now to FIG. 1, the present invention may be assembled by providing a generic disposable baby diaper (1), and attaching a folded powder patch (2), to said diaper by using an adhesive film applied to a back pad side of said powder patch. A pad cover (3), may be placed over a priming area (4), of a front pad of said powder patch by a weak bonding adhesive to facilitate the easy removal of said pad cover and thereby exposing said priming area to the atmosphere. Said front pad must form a continuous boundary when sealed to said back pad to contain a powder substance (5) disposed therebetween and communicating with said pad cover via a number of openings in said priming area. Said powder patch may be placed near the waist area of said baby diaper, having said priming area situated away from said baby diaper.

The present invention may be operated by removing said pad cover (3), from said priming area (4), and folding said baby diaper at the crouch area and patting both sides of said baby diaper together, to facilitate the release of said powder substance (5), into said folded baby diaper. Once said powder substance is released, said baby diaper may be re-opened and applied to a wearer.

In conclusion, note that the present invention may be constructed of any materials that will allow its correct operation and that is compatible with its wearer. Also, notice that a powder patch formed from two adjacent integral diaper layers, and sealed around designated pad perimeters, having the surface layer contain a priming area, may be the most economical method of manufacturing the present invention.

What is claimed is:

1. A dispensing system comprising a diaper and a pocket patch including a substance wherein the pocket patch is connected with and adapted to dispense the substance to a surface of the diaper for receiving bodily waste and wherein the pocket patch is located about a waist of the diaper.

2. A dispensing system comprising a diaper and a pocket patch including a substance wherein the pocket patch is connected with and adapted to dispense the substance to a surface of the diaper for receiving bodily waste and wherein the pocket patch further includes a priming area for providing means of dispensing the substance to the surface of the diaper adapted to receive bodily waste and an adhesive pad cover connected with the priming area.

3. The dispensing system according to claim 2 wherein the pocket patch further includes a front pad and a back pad connected with the front pad to provide a continuous boundary, the priming area being located within the front pad.

4. A method of dispensing a substance to a diaper surface adapted to receive bodily waste comprising providing the powder dispensing system of claim 2; folding the diaper about a crotch area thereof; removing the adhesive pad cover from the priming area; and patting the diaper to facilitate dispensing of the substance.

5. A method of dispensing a substance to a diaper surface adapted to receive bodily waste comprising providing a dispensing system including a diaper and a pocket patch including the substance wherein the pocket patch is connected with and adapted to dispense the substance to the surface of the diaper for receiving bodily waste; folding the diaper about a crotch area thereof; and patting the diaper to facilitate dispensing of the substance.

6. A method of dispensing a substance to a diaper surface adapted to receive bodily waste comprising providing a diaper including a first layer, a second layer, a pocket void arranged between the first layer and the second layer for containing the substance and means of dispensing the substance from the pocket void to the surface of the diaper adapted to receive bodily waste; folding the diaper about a crotch area thereof; and patting the diaper to facilitate dispensing of the substance.

7. A method of dispensing a substance to a diaper surface adapted to receive bodily waste comprising providing a diaper including a first layer, a second layer, a pocket void arranged between the first layer and the second layer for containing the substance, means of dispensing the substance from the pocket void to the surface of the diaper adapted to receive bodily waste, and an adhesive pad cover connected with the diaper for preventing the substance from dispensing; folding the diaper about a crotch area thereof; removing the adhesive pad cover from the diaper and patting the diaper to facilitate dispensing of the substance.

* * * * *